(12) United States Patent
de Wild et al.

(10) Patent No.: US 11,801,032 B2
(45) Date of Patent: Oct. 31, 2023

(54) ULTRASOUND PROBE, USER CONSOLE, SYSTEM AND METHOD

(71) Applicant: KONINKLIJKE PHILIPS N.V., Eindhoven (NL)

(72) Inventors: Nico Maris Adriaan de Wild, Eindhoven (NL); Hendrikus Hubertus Maria Korsten, Eindhoven (NL); Arthur Bouwman, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/915,202

(22) PCT Filed: Mar. 30, 2021

(86) PCT No.: PCT/EP2021/058244
§ 371 (c)(1),
(2) Date: Sep. 28, 2022

(87) PCT Pub. No.: WO2021/198226
PCT Pub. Date: Oct. 7, 2021

(65) Prior Publication Data
US 2023/0113291 A1    Apr. 13, 2023

(30) Foreign Application Priority Data

Apr. 2, 2020    (EP) .................... 20167730.9

(51) Int. Cl.
*A61B 8/08* (2006.01)
*A61B 8/00* (2006.01)

(52) U.S. Cl.
CPC .......... *A61B 8/0841* (2013.01); *A61B 8/4444* (2013.01); *A61B 8/462* (2013.01)

(58) Field of Classification Search
CPC ...... A61B 8/0841; A61B 8/4444; A61B 8/462
See application file for complete search history.

(56) References Cited

U.S. PATENT DOCUMENTS

| 5,997,479 A | 12/1999 | Savord et al. |
| 6,013,032 A | 1/2000 | Savord |

(Continued)

FOREIGN PATENT DOCUMENTS

| JP | H11299778 A | 11/1999 |
| JP | 2007159651 A | 6/2007 |

(Continued)

OTHER PUBLICATIONS

International Search Report and Written Opinion for PCT/EP2021/058244; dated Jun. 9, 2021, 9 pages.

(Continued)

*Primary Examiner* — Yi-Shan Yang
*Assistant Examiner* — Nicholas A Robinson

(57) ABSTRACT

An ultrasound probe (10) is disclosed comprising a plurality of transducer elements (66) within a housing (60) and arranged proximal to a subject contact surface (65) of the probe; a plurality of individually addressable light sources (72) mounted in said housing, each of said individually addressable light sources indicating a position of a subset of the plurality of transducer elements relative to said subject contact surface; and a controller (80) arranged to control said plurality of individually addressable light sources in response to a light source selection signal from an ultrasound user console (3). Also disclosed is such an ultrasound user console (3), an ultrasound imaging system (1) comprising the ultrasound probe (10) and the ultrasound user console (3) as well as a method (100) of marking the location of an anatomical feature (7) within a subject with such an ultrasound imaging system (1).

14 Claims, 7 Drawing Sheets

(56) References Cited

U.S. PATENT DOCUMENTS

| | | |
|---|---|---|
| 6,283,919 B1 | 9/2001 | Roundhill et al. |
| 6,443,896 B1 | 9/2002 | Detmer |
| 6,458,083 B1 | 10/2002 | Jago et al. |
| 6,530,885 B1 | 3/2003 | Entrekin et al. |
| 2012/0136256 A1 | 5/2012 | Nozaki et al. |
| 2015/0057546 A1 | 2/2015 | Yoon et al. |
| 2015/0148664 A1 | 5/2015 | Stolka et al. |
| 2020/0088872 A1 | 3/2020 | Luo et al. |

FOREIGN PATENT DOCUMENTS

| | | |
|---|---|---|
| JP | 2008253578 A | 10/2008 |
| JP | 2014087560 A | 5/2014 |
| JP | 2014087560 A1 | 5/2014 |
| WO | 2006005351 A1 | 1/2006 |
| WO | 2019016343 A1 | 1/2019 |
| WO | WO-2019016343 A1 * | 1/2019 |

OTHER PUBLICATIONS

"Guidance on the use of ultrasound locating devices for placing central venous catheters",National Institute for Clinical Excellence, 2002, 32 pages.

Rothschild, J.M. et al., "Ultrasound Guidance of Central Vein Catheterization", Agency for Healthcare Research and Quality (USA), Evidence Report/Technology Assessment No. 43, 2001, Chapter 21, 11 pages.

Rafie, I.M. et al, "Patients undergoing PCI from the femoral route by default radial operators are at high risk of vascular access-site complications", EuroIntervention, 2014, vol. 9, pp. 1189-1194.

Jolly, S.S. et al., "Radial versus femoral access for coronary angiography and intervention in patients with acute coronary syndromes (RIVAL): a randomized, parallel group, multicenter trial", Lancet, 2011, vol. 377, pp. 1409-1420.

Seto, A.H., Real-time ultrasound guidance facilitates transradial access: RAUST (Radial Artery access with Ultrasound Trial), JACC Cardiovasc Interv., 2015, vol. 8, pp. 283-291.

Shiloh, A. et al., "Ultrasound-guided catheterization of the radial artery: a systematic review and metanalysis of randomized controlled trials", Chest, 2011, vol. 139, pp. 524-529.

Yeow, K.M. et al., "Sonographically guided antegrade common femoral artery access", J Ultrasound Med., 2002, vol. 21, pp. 1413-1416.

Kweon, M. et al., "Antegrade superficial femoral artery versus common femoral artery punctures for infrainguinal occlusive disease", J Vasc Interv Radiol, 2012, vol. 23, pp. 1160-1164.

Yilmaz, S. et al., "Ultrasound-guided retrograde popliteal artery catheterization: experience in 174 consecutive patients", J Endovasc Ther, 2005, vol. 12, pp. 714-722.

Seto, A. et al, "Ultrasound-Guided Arterial Access Is the Way to Go. Vascular access using ultrasound is safe and efficient", Cardiac Interventions Today, 2012, pp. 58-62.

* cited by examiner

ULTRASOUND PROBE, USER CONSOLE, SYSTEM AND METHOD

This application is the U.S. National Phase application under 35 U.S.C. § 371 of International Application No. PCT/EP2021/058244 filed on Mar. 30, 2021, which claims the benefit of European Application 20167730.9, filed Apr. 2, 2020. These applications are hereby incorporated by reference herein.

FIELD OF THE INVENTION

The present invention relates to an ultrasound probe comprising a plurality of transducer elements within a housing and arranged proximal to a patient contact surface of the probe.

The present invention further relates to an ultrasound user console comprising a processor arrangement adapted to convert ultrasound echo signals received by the plurality of ultrasound transducers of such an ultrasound probe into an ultrasound image, a display device under control of said processor arrangement and adapted to display said ultrasound image and a user interface communicatively coupled to the processor arrangement and adapted to allow a user to mark a region of the displayed ultrasound image.

The present invention further relates to an ultrasound imaging system comprising such an ultrasound probe and ultrasound user console.

The present invention further relates to a method of marking the location of an anatomical feature within a patient with such an ultrasound imaging system.

BACKGROUND OF THE INVENTION

Placement of (minimally) invasive medical devices such as needles and catheters for procedures like vascular access, biopsies, nerve blocks and so on can be challenging, as the correct entry point for such devices into the patient's anatomy may be difficult to establish. Incorrect entry points of such devices are highly undesirable as the consequential multiple attempts to correctly insert such devices are stressful to the patient and increase the risk of complications of such procedures, e.g. increased risk of infections and so on.

Ultrasound guidance has emerged as a valuable tool for the placement of needles and catheters. The advantages of ultrasound guidance include real-time visualization of landmarks, improved pre-procedure planning, reduction in complications, less time spent by a physician at the patient's bedside and improved first-attempt needle or catheter entry success rates. In particular, ultrasound guidance has emerged as a valuable tool for needle-based interventions, such as biopsies, vascular access, prostate biopsy and so on. This is attractive because ultrasound imaging systems are currently readily available and widely utilized in many emergency departments, radiology departments, operating rooms, and ICUs, to name but a few.

However, ultrasound physics and transducer properties may introduce artefacts that challenge the success of ultrasound guided procedures. These artefacts especially become important in case of small targets, such as the radial artery, peripheral veins or small tumours such as breast and thyroid tumours. Missing a target requires a redirection of the needle and increases the risk of complications or even failure of the procedure, e.g. because of failure to establish vascular access or obtain a reliable biopsy. The radial artery for instance is small and is difficult to locate in patients with hypotension, shock, atherosclerosis and obesity. Hence, although by utilizing ultrasound guidance the success rate of such procedures has increased, while the procedure time, the amount of needle redirections and complications has reduced, there is still room for improvement.

When using such ultrasound guidance, basic B-mode imaging may be used starting in the transverse or short axis view to see the cross section of the target anatomical feature of the patient. In a short-axis view, the image plane is perpendicular to the course of the needle, i.e. the needle is "out of plane", which is visualized as a hyperechoic point in the cross section. In a long-axis view, the image plane is parallel to the course of this target anatomical feature and the needle, i.e., the needle is "in plane". The image should show the course of the shaft and point of the needle as it is advanced towards the target. For the out of plane approach, the physician orients the target anatomical feature of the patient exactly in the centre of the ultrasound screen by repositioning of the ultrasound (US) probe. With the US probe centered exactly over the target anatomical feature, the needle should be placed a few mm distal of the probe and keeping it exactly in line with the centre of the transducer. The needle (bright white dot) should now appear as a bright white dot in the ultrasound image over the centre of the target anatomical feature of the patient. If this is not the case, the physician redirects the needle while advancing either further or by withdrawing.

This procedure, however, is not without problems. Although fixed markers on ultrasound transducers are used to guide operators, currently there is no real-time physical reference between the position of the target in the ultrasound screen and the position over the length of the transducer, making it more difficult for the practitioner to correctly position the needle over the patient's anatomical feature of interest.

JP 2014-087560 A discloses a probe guide device in which an ultrasound probe can be linearly moved. The probe guide device includes a probe position detection unit that detects the position of a probe; a probe movement support unit which serves as rails for linearly moving the probe and makes LEDs emit light; an LED array disposed on the frame of the probe movement support unit and a probe case to which the probe inserted by an operator is held. Tissue of interest is extracted from volume data by an ultrasonic diagnostic apparatus and the distribution of the tissue of interest is shown by a light emission pattern of the LED array. In this manner, tissue of interest can be highlighted with the LEDs on the probe guide device by linearly moving the ultrasound probe across an anatomical region of interest within the probe guide device. This however lacks the desired granularity for highlighting small anatomical features, such as anatomical features having a diameter or cross-section that is smaller than the width of the ultrasound probe, for which (large) linear movement of the ultrasound probe often is unnecessary.

WO 2019/016343 discloses an ultrasound probe in which two or more imaging planes are generated, using respective linear arrays. Light diodes on the probe are arranged to indicate the linear array that is currently transmitting or receiving an ultrasound signal.

SUMMARY OF THE INVENTION

The present invention seeks to provide an ultrasound probe comprising a plurality of transducer elements within a housing and arranged proximal to a patient (a subject, a person, an individual) contact surface of the probe that can highlight the position of an anatomical feature of interest relative to the probe such that a physician can more accurately access the anatomical feature of interest.

The present invention further seeks to provide an ultrasound user console arranged to control such an ultrasound probe.

The present invention further seeks to provide an ultrasound imaging system including such an ultrasound user console and ultrasound probe.

The present invention further seeks to provide a method of marking the location of an anatomical feature within a patient with such an ultrasound imaging system.

According to an aspect, there is provided an ultrasound probe comprising a plurality of transducer elements within a housing and arranged proximal to a patient contact surface of the probe; a plurality of individually addressable light sources mounted in said housing, each of said individually addressable light sources indicating a position of a subset of the plurality of transducer elements relative to said patient contact surface; and a controller arranged to control said plurality of individually addressable light sources in response to a light source selection signal from an ultrasound user console.

Preferable, the light source selection signal identifies an ultrasound transducer or a scan line of ultrasound transducers from said plurality of ultrasound transducers responsible for generating a user-marked region of a displayed ultrasound image. The light sources are for example controlled to output the position of the identified ultrasound transducer or scan line relative to the patient contact surface of said probe.

With such an ultrasound probe, the location of a patient's anatomical feature of interest relative to the position of the ultrasound probe on the patient's body can be accurately flagged by switching on the light source located over said anatomical feature of interest. As will be explained in further detail below, the appropriate light source can be identified by a processor arrangement processing the ultrasound image data produced by the ultrasound transducers of the ultrasound probe, e.g. by a user highlighting the anatomical feature of interest in an ultrasound image generated by the processor arrangement from such ultrasound image data and the processor arrangement identifying the ultrasound transducer(s) and associated light source(s) responsible for generating the ultrasound image data responsible for imaging the highlighted anatomical feature of interest.

Hence, the thus switched on light source provides a clear visible marker on the ultrasound probe that aids a physician in correctly positioning a needle or the like for insertion into the anatomical feature of interest of the patient, e.g. proximal to the switched on light source.

Preferably, the individually addressable light sources are LEDs (light emitting diodes) as LEDs are robust and energy-efficient, for instance. Each or any of such LED(s) may, for instance, comprise inorganic LED(s) and/or organic LED(s) (OLED(s)).

Preferably, each individually addressable light source indicates the position of a single transducer element or single scan line of transducer elements relative to said patient contact surface such that a particularly fine-grained marking of the anatomical feature of interest may be achieved with the light sources.

In an embodiment, the plurality of transducer elements and the individually addressable light sources each are arranged in a 1-dimensional array. Alternatively, the plurality of transducer elements and the individually addressable light sources each are arranged in a 2-dimensional array.

In a preferred embodiment, the individually addressable light sources are arranged proximal to said patient contact surface on a side surface of the housing such that the light sources are arranged close to the patient's skin when the ultrasound probe is positioned thereon, thus further aiding the accurate positioning of a needle or the like on the patient's skin in alignment with the illuminated light source.

Alternatively, the ultrasound probe is a patch and the individually addressable light sources are arranged on a portion of the housing surrounding and in the plane of said patient contact surface such that the illuminated light source can be seen along the edge of the patch, thereby assisting the physician in the correct positioning of the needle or the like on the patient's skin.

According to another aspect, there is provided an ultrasound user console comprising a processor arrangement adapted to convert ultrasound echo signals received by the plurality of ultrasound transducers of the ultrasound probe of any of the herein described embodiments into an ultrasound image; a display device under control of said processor arrangement and adapted to display said ultrasound image; and a user interface communicatively coupled to the processor arrangement and adapted to allow a user to mark a region of the displayed ultrasound image, wherein the processor arrangement further is adapted to identify an ultrasound transducer or a scan line of ultrasound transducers from said plurality of ultrasound transducers responsible for generating the marked region of the displayed ultrasound image and generate a light source selection signal for the light source of said ultrasound probe indicating the position of the identified ultrasound transducer or scan line relative to the patient contact surface of said probe.

In an embodiment, the user interface is adapted to allow said user to mark said region by drawing a line across said region. This allows for a straightforward and intuitive marking of the region of interest by the user.

The user interface further may be adapted to allow a user to mark a further region of the displayed ultrasound image, in which case the processor arrangement further may be adapted to identify a further ultrasound transducer or a further scan line of ultrasound transducers from said plurality of ultrasound transducers responsible for generating the marked further region of the displayed ultrasound image; and generate a further light source selection signal for the further light source of said ultrasound probe indicating the position of the identified further ultrasound transducer or said further scan line relative to the patient contact surface of said probe. This for instance may be used by the user to mark opposite edges of the anatomical feature of interest, such that the correspondingly illuminated light sources on the ultrasound probe illuminate the boundaries or edges of the anatomical feature of interest, thereby guiding the physician to position the needle for insertion into the anatomical feature of interest in between the illuminated light sources.

In a further embodiment, the processor arrangement further is adapted to convert further ultrasound echo signals received by the plurality of ultrasound transducers of the ultrasound probe of any of the herein described embodiments into a further ultrasound image;

identify the marked region in the further ultrasound image;

identify an ultrasound transducer or a scan line of ultrasound transducers from said plurality of ultrasound transducers responsible for generating the marked region of the further ultrasound image; and generate a further light source selection signal for the light source of said ultrasound probe indicating the position of the identified ultrasound transducer or scan line of ultrasound transducers responsible for generating the marked region of the further ultrasound image relative to the patient contact surface of said probe. This has the advantage that the clinician can make small adjustments to the position of the ultrasound probe on the patient's body without having to reselect the feature(s) of interest due to the automatic tracking of this feature in further ultrasound images and corresponding light source activation to show the (adjusted) location of the region of interest relative to the patient contact surface of the ultrasound probe. Such automated tracking may be applied to a single marked region such as a vessel centre line as well as to a plurality of marked regions such as opposing vessel walls for example.

Preferably, the displayed ultrasound image is a B-mode ultrasound image as this typically facilitates a particularly straightforward identification of the anatomical feature of interest in the ultrasound image.

According to yet another aspect, there is provided an ultrasound imaging system comprising the ultrasound probe and the ultrasound user console of any of the herein described embodiments. Such an ultrasound imaging system can be used by a physician to aid him or her with in the correct positioning of a needle or the like on a patient's body relative to an anatomical feature of interest, thereby significantly reducing the risk of the need for multiple needle insertions.

According to yet another aspect, there is provided a method of marking the location of an anatomical feature within a patient, the method comprising positioning the ultrasound probe of any of the herein described embodiments on a part of the anatomy of said patient including said anatomical feature and generating ultrasound image data of said part of the anatomy with said ultrasound probe; generating an ultrasound image from said ultrasound image data and displaying said ultrasound image with the ultrasound user console of any of the herein described embodiments; receiving a marker marking part of said anatomical feature in said ultrasound image from the user interface of said ultrasound user console; identifying an ultrasound transducer or a scan line of ultrasound transducers from said plurality of ultrasound transducers responsible for generating the marked part of the anatomical feature in the displayed ultrasound image; generating a light source selection signal for the light source of said ultrasound probe indicating the position of the identified ultrasound transducer or scan line relative to the patient contact surface of said probe; and switching on said light source in response to said generated light source selection signal. Such a method facilitates the correct position of the needle or the like on the patient's body for insertion into the anatomical feature of interest, thereby significantly reducing the risk of the insertion of such a needle or the like missing the anatomical feature of interest.

In an embodiment, the marked part of said anatomical feature approximates a centre line of said anatomical feature, such as the centre line of a blood vessel, tumour or the like in order to maximise the likelihood of a needle or the like being inserted into the anatomical feature of interest.

Alternatively, the marked part of said anatomical feature approximates an edge of said anatomical feature, with the method further comprising receiving a further marker marking an approximate opposite edge of said anatomical feature in said ultrasound image from the user interface of said ultrasound user console; identifying a further ultrasound transducer or further scan line of ultrasound transducers from said plurality of ultrasound transducers responsible for generating said approximate opposite edge of the anatomical feature in the displayed ultrasound image; generating a further light source selection signal for the further light source of said ultrasound probe indicating the position of the identified further ultrasound transducer or further scan line relative to the patient contact surface of said probe; and switching on said further light source in response to said generated further light source selection signal. This way, the opposite edges or boundaries of the anatomical feature of interest are marked by the illuminated light sources, such that the physician can position the needle or the like for correct insertion into the anatomical feature of interest in between the pair of illuminated light sources marking the approximated opposite edges or boundaries of the anatomical feature of interest.

In an embodiment, the method further comprises, with said processor arrangement, converting further ultrasound echo signals received by the plurality of ultrasound transducers of the ultrasound probe of any of the herein described embodiments into a further ultrasound image; identifying the marked region in the further ultrasound image; identifying an ultrasound transducer or a scan line of ultrasound transducers from said plurality of ultrasound transducers responsible for generating the marked region of the further ultrasound image; and generating a further light source selection signal for the light source of said ultrasound probe indicating the position of the identified ultrasound transducer or scan line of ultrasound transducers responsible for generating the marked region within the further ultrasound image relative to the patient contact surface of said probe. Such automated feature tracking may be applied to single marked regions or multiple marked regions in the ultrasound image marked by the user, as previously explained.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
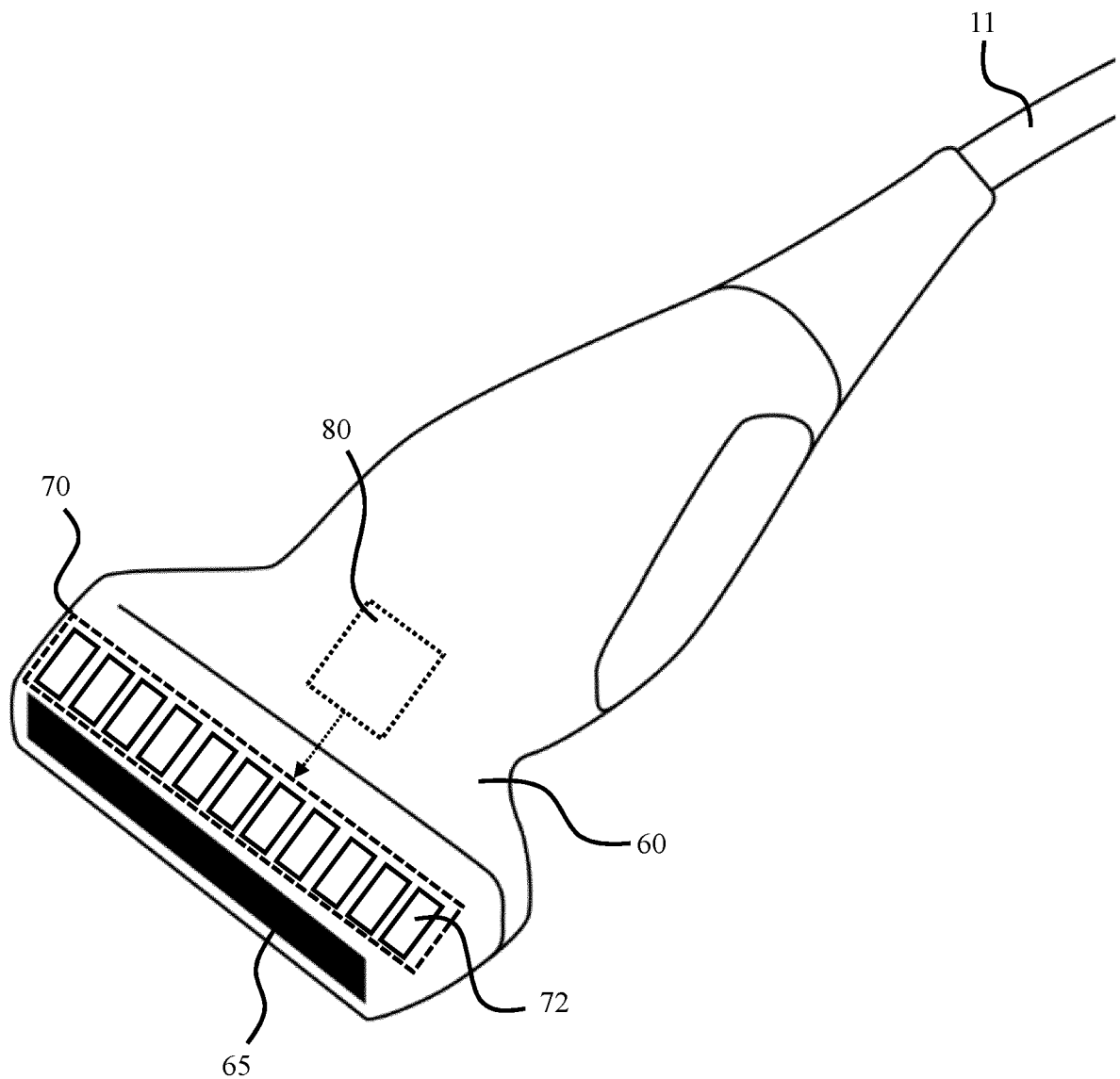
FIG. 1 schematically depicts an ultrasound probe according to an embodiment.

It should be understood that the Figures are merely schematic and are not drawn to scale. It should also be understood that the same reference numerals are used throughout the Figures to indicate the same or similar parts.

FIG. 1 schematically depicts an ultrasound probe 10 according to an embodiment of the present invention in perspective view. The ultrasound probe 10 typically comprises a plurality of transducer elements (not visible in FIG. 1) within a housing 60. The transducer elements typically are arranged proximal to a patient contact surface 65 of the ultrasound probe 10 such that ultrasound waves generated by the transducer elements can be transmitted into a patient's body through the patient contact surface 65 and echo signals from the patient's body may be received by the transducer elements through the patient contact surface 65. The transducer elements may form at least part of the patient contact surface 65, or the patient contact surface 65 may comprise one or more layers covering the transducer elements, e.g. an acoustic matching layer, an electrically insulating layer, a cover layer, and so on. Such arrangements are well-known to the skilled person and will therefore not be explained in further detail for the sake of brevity only. Any suitable arrangement of the patient contact 65 may be used.

The housing 60 further comprises an array 70 of individually addressable light sources 72 mounted in the housing 70. The light sources 72 may take any suitable shape although preferably the light sources 72 are LEDs, as LEDs are robust and energy efficient, as well as generate little heat, which is beneficial when operating the ultrasound probe 10. Each of the individually addressable light sources 72 indicates a position of a subset of the plurality of transducer elements relative to the patient contact surface 70, such as an individual transducer element or an individual scan line of transducer elements, i.e. a line or array of transducer elements responsible for the generation of a single line in the ultrasound image. More specifically, each of the transducer elements produces ultrasound signal data, which data signals are processed to form an ultrasound image, preferably a B-mode image, as will be explained in further detail below. The ultrasound data of each transducer element is responsible for the generation of a discrete region or portion of such an ultrasound image, which image region or portion upon selection by a user may be highlighted on the ultrasound probe 10 by switching on, i.e. illuminating, the corresponding light source 72. In this manner, a marker in the form of an illuminated light source 72 can be produced directly above the imaged region, e.g. of an anatomical feature of a patient such as a blood vessel, tumour or the like, such that a physician can place an invasive instrument such as a needle or the like on the skin of the patient in alignment with the illuminated light source 72, thereby ensuring that the invasive instrument is correctly positioned relative to the anatomical feature of interest. This will be explained in further detail below. For this reason, the array 70 of light sources 72 preferably is located as close as possible to the patient contact surface 65, i.e. proximal to this surface, on or in a side surface of the housing 60 to aid such alignment as effectively as possible. Moreover, each light source 72 preferably identifies a single transducer element (or single scan line of transducer elements) to maximize the granularity of the anatomical feature highlighting with the light sources 72.

The ultrasound probe further comprises a controller 80 within the housing 60 that is arranged to control the plurality of individually addressable light sources 72 in response to a light source selection signal from an ultrasound user console 3 as will be explained in further detail below. Such a light source selection signal may be provided to the controller 80 in any suitable manner, e.g. through the probe cable 11, which probe cable typically communicatively couples the ultrasound probe 10 to the ultrasound user console 3. Upon receiving the light source selection signal, the controller 80 switches on the light source 72 identified in the light source selection signal. The controller 80 may further receive a light source deselection signal from the ultrasound user console 3 in order to switch off the previously selected light source 72, for example upon a physician indicating through the ultrasound user console 3 that the anatomical feature of interest has been successfully accessed.

Figure 2:
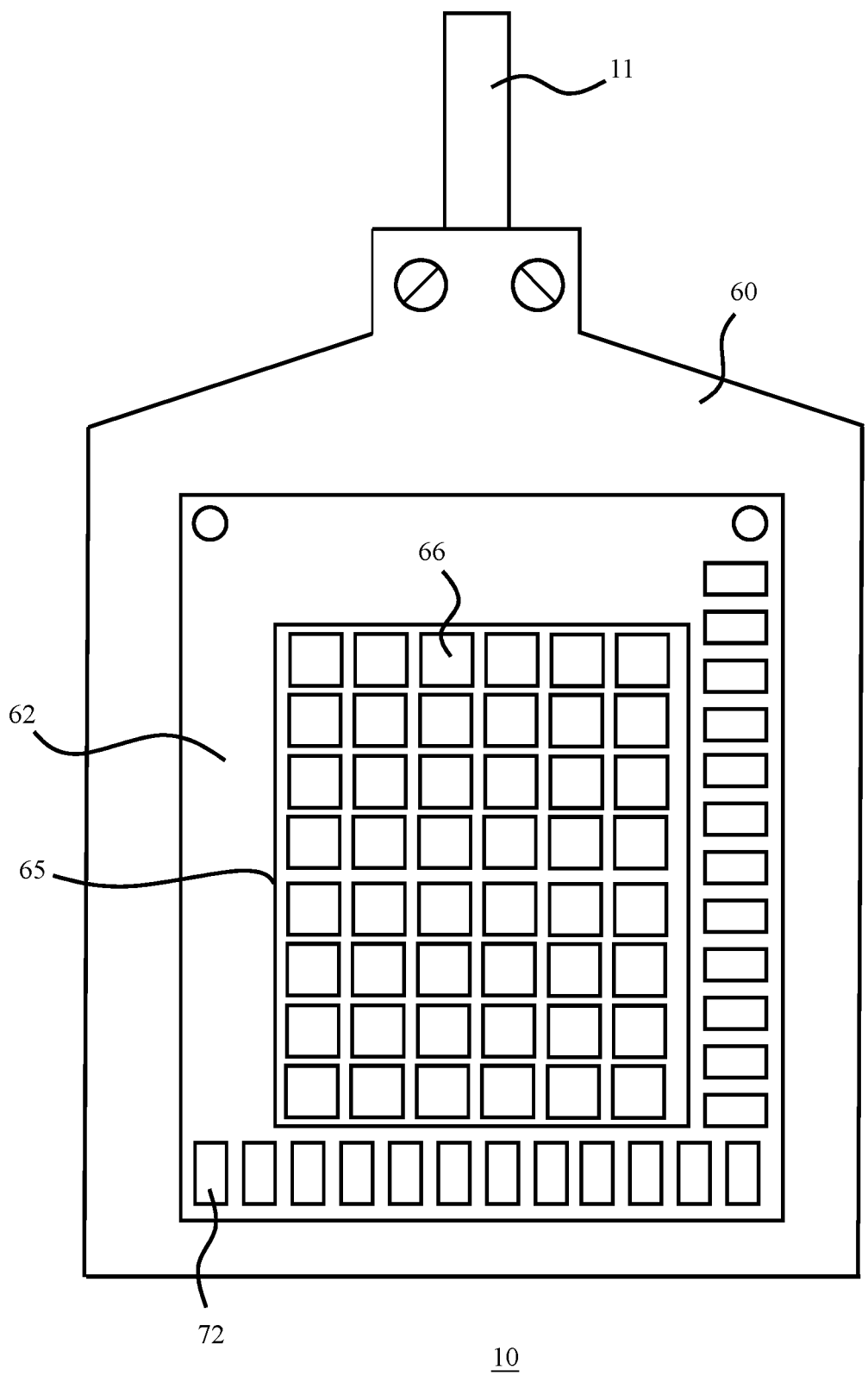
FIG. 2 schematically depicts an ultrasound probe according to another embodiment.

The ultrasound probe 10 may take any suitable shape. For example, the ultrasound probe 10 may be a handheld probe or alternatively may be mounted in a probe holder to allow hands-free operation of the probe, which for instance may be advantageous where the physician is to perform an invasive procedure on the patient, as previously explained. The ultrasound probe 10 may have 2-D imaging capability, e.g. in which the plurality of transducer elements and the individually addressable light sources 72 each are arranged in a 1-dimensional array, or may have 3-D imaging capability, in which the plurality of transducer elements and the individually addressable light sources each are arranged in a 2-dimensional array. FIG. 2 schematically depicts an ultrasound probe 10 in the form of a patch, in which the patient contact surface 65 comprises a 2-D array of ultrasound transducer elements 66 and the light sources 72 are arranged as a 2-D array, i.e. two 1-D arrays under a perpendicular angle to each other along two sides, i.e. on both axes, of the patient contact surface 65 on a portion 62 of the housing 60 lying in the same plane as the patient contact surface 65. Such a patch may comprise an adhesive area (not shown) for adhering the patch to a region of the patient's skin for hands-free operation as is well-known per se.

Figure 3:
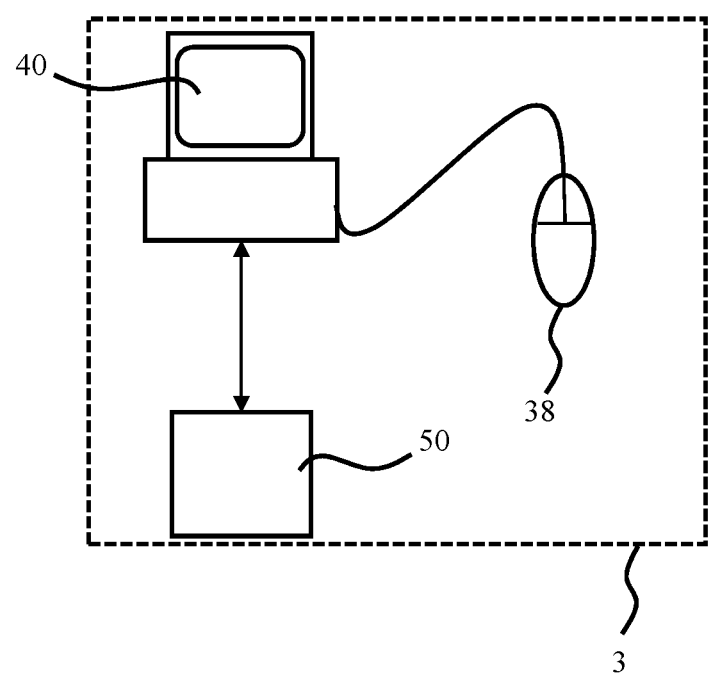
FIG. 3 schematically depicts an ultrasound user console according to an embodiment.

FIG. 3 schematically depicts an ultrasound user console 3 according to an embodiment of the present invention. The ultrasound user console 3 comprises a processor arrangement 50, which arrangement may comprise one or more discrete processors, which functionality will be described in further detail below. Where reference is made to different types of processors, it should be understood that such processors may be discrete physical entities or may be different functions performed by a single processor. The processor arrangement 50 typically is to convert ultrasound echo signals received from the plurality of ultrasound transducers 66 of the ultrasound probe 10 through the probe cable 11 into an ultrasound image such as a B-mode image for example in some embodiment and to control a display device 40 to display the generated ultrasound image. The processor arrangement 50 may be located in a housing that also houses the display device 40, or may be located in a different entity communicatively coupled to the display device 40, e.g. through a cable or the like.

The ultrasound user console 3 further comprises a user interface 38 communicatively coupled to the processor arrangement 50. Such a user interface 38 may take any suitable form, e.g. a peripheral device such as a mouse or trackball, a keyboard, a touch screen arrangement, a speech recognition system, and so on, or any combination of such user interface entities. As will be explained in further detail below, the user interface 38 allows a user of the ultrasound user console 3 to select or mark a region of the displayed ultrasound image, such as a region of the displayed ultrasound image in which an edge or centre of an anatomical feature of interest of the patient is located. The processor arrangement 50 is further adapted to identify the ultrasound transducer 66 from the plurality of ultrasound transducers that is responsible for generating the region of the displayed ultrasound image marked by the user and generate a light source selection signal for the light source 72 of the ultrasound probe 10 indicating the position of the identified ultrasound transducer 66 relative to the patient contact surface 65 of the ultrasound probe 10, which light source selection signal is transmitted to the controller 80 of the light sources 72, e.g. through the probe cable 11.

The ultrasound user console 3 may take any suitable shape, e.g. a patient monitor or the like, in which all elements of the user console 3 are integrated into a single housing unit, or may take a more distributed form in which at least some of the elements of the user console 3 are in different housing units and communicatively coupled to each other in a wired or wireless fashion. Alternatively, the ultrasound user console 3 may take the shape of a portable device such as a tablet computer, laptop computer, smartphone or the like, to which the ultrasound probe 10 may be coupled, e.g. in a wired fashion by a probe cable 11 connecting the ultrasound probe 10 to such a portable device. In yet another embodiment, the ultrasound user console 3 may be implemented as a distributed system, e.g. by at least part of the processor arrangement 50 being cloud-based, in which case the ultrasound data may be provided to the processor arrangement for processing over a network connection such as the Internet.

Figure 4:
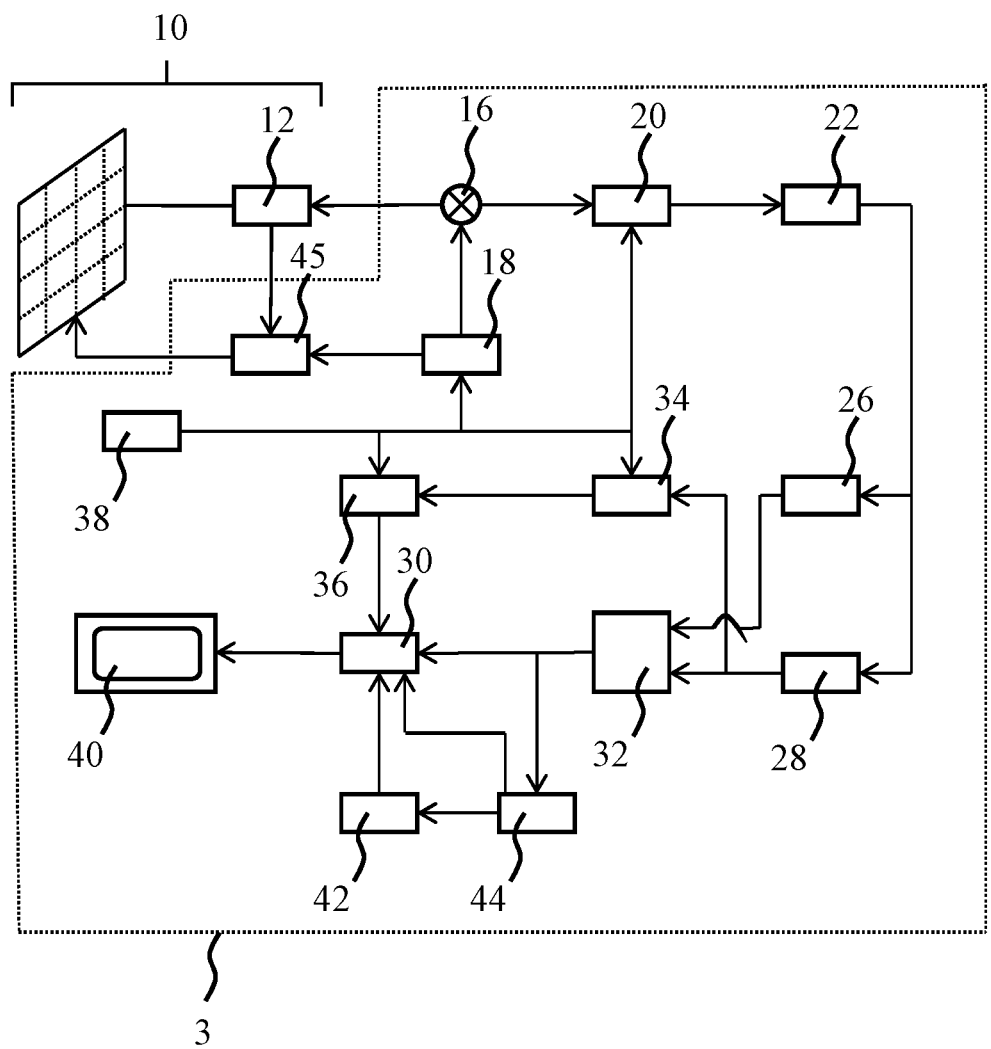
FIG. 4 schematically depicts an ultrasound imaging system according to an example embodiment.

FIG. 4 schematically depicts an example embodiment of an ultrasound imaging system 1 with an ultrasound probe 10, e.g. an array of ultrasound transducer elements 66, which may be arranged in a one-dimensional or two-dimensional array of transducer elements as previously explained. Any suitable type of ultrasound transducer elements 66 may be used for this purpose, e.g. piezoelectric transducer (PZT) elements, capacitive micro-machined ultrasound transducer (CMUT) elements, piezoelectric micro-machined transducer (PMUT) elements, and so on, although CMUT elements are particularly preferred, in particular over (PZT) elements due to their superior (adjustable) resonance frequency range, which make CMUT elements particularly suitable for patient monitoring purposes. As such transducer elements are well-known per se, they will not be explained in further detail for the sake of brevity only. Where reference is made to an ultrasound transducer element, it should be understood that this refers to a transducer unit addressable by a single control signal. This may be a single transducer cell or a cluster, e.g. tile, of transducer cells arranged to operate in unison, i.e. as a single element. The array of transducer elements may be arranged as a phased array to facilitate beam steering of an ultrasound beam generated with the ultrasound probe 10. Again, such beam steering is well-known per se and will not be explained in further detail for the sake of brevity only.

The ultrasound probe 10 typically is operable in a transmit mode in which ultrasound beams are generated and a receive mode in which the ultrasound probe 10 is operable to receive echo signals induced by the generated ultrasound beams within the body of the individual being imaged with the ultrasound probe 10. The ultrasound probe 10 typically is controlled by an ultrasound user console 3, and may be communicatively coupled thereto in any suitable manner, e.g. through a (coaxial) cable 11 or the like.

The ultrasound probe 10 may be coupled to a microbeam former 12, which may be integrated in the ultrasound probe 10, which controls transmission and reception of signals by the ultrasound transducer elements (or clusters thereof) of the ultrasound probe 10. Microbeam formers are capable of at least partial beam forming of the signals received by groups or "patches" of transducer element tiles for instance as described in U.S. Pat. No. 5,997,479 (Savord et al.), U.S. Pat. No. 6,013,032 (Savord), and U.S. Pat. No. 6,623,432 (Powers et al.). The microbeam former 12 may be coupled by a probe cable 11, e.g. coaxial wire, to the ultrasound user console 3, e.g. a patient interface module or the like, comprising a transmit/receive (T/R) switch 16 which switches between transmission and reception modes and protects the main beam former 20 from high energy transmit signals when a microbeam former is not present or used and the ultrasound probe 10 is operated directly by the main system beam former 20. The transmission of ultrasonic beams from the ultrasound probe 10 under control of the microbeam former 12 may be directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the ultrasound probe 10, or at different angles for a wider field of view. The transducer controller 18 may be coupled to control the voltage source 45 for the ultrasound probe 10. For instance, the power supply 45 may set the DC and AC bias voltage(s) that are applied to CMUT cells in case of a CMUT probe 10, e.g. to operate the one or more CMUT cells of the CMUT elements in collapse mode, as is well-known per se.

The partially beam-formed signals produced by the microbeam former 12 may be forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of ultrasound transducer cells. In this way the signals received by thousands of transducer cells of a transducer array 10 can contribute efficiently to a single beam-formed signal.

The beam-formed signals are coupled to a signal processor 22, which may form part of the processor arrangement 50 of the ultrasound user console 3 by way of non-limiting example only. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be forwarded to a B-mode processor 26 and optionally to a Doppler processor 28, which processors also may form part of the processor arrangement 50. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44, both which may also form part of the processor arrangement 50. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42, which also may form part of the processor arrangement 50, converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 forming part of the processor arrangement 50 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user interface or control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface or control panel 38, such as patient name.

The user interface may also be coupled to the transmit controller 18 to control the generation of ultrasound signals from the ultrasound probe 10 and hence the images produced by the transducer array and the ultrasound system. The user interface may also be coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasound imaging system 1 is intended to give a non-limiting example of such an ultrasonic diagnostic imaging system. The skilled person will immediately realize that several variations in the architecture of the ultrasound imaging system 1 are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Furthermore, where reference is made to different processor entities forming part of the processor arrangement 50, it should be understood that such processors may be discrete hardware devices or at least some of these processor entities may be combined into a single processor architecture performing the different functions of these respective processor entities. Other variations will be apparent to the skilled person.

Figure 5:
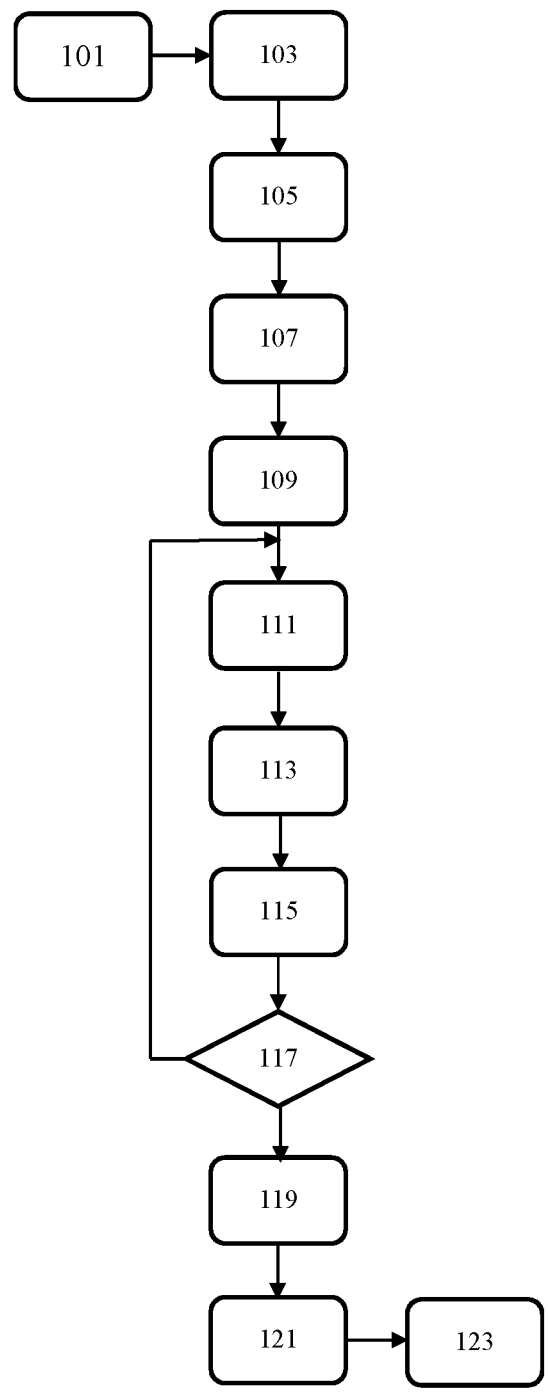
FIG. 5 schematically depicts a flowchart of a method according to an embodiment.

FIG. 5 is a flowchart of an embodiment of a method 100 for marking the location of an anatomical feature within a patient with the ultrasound imaging system 1 by enabling one or more light sources 72 on the ultrasound probe 10 as previously explained. The method 100 starts in operation 101, after which the method 100 proceeds to operation 103 in which the ultrasound probe 10 is placed on a body region of the patient such as to obtain an ultrasound image of an anatomical feature of interest within the patient's body, e.g. a blood vessel, tumour or the like. Once the ultrasound probe 10 has been positioned on the patient's body, ultrasound data may be generated with the ultrasound probe 10 in operation 105. The captured data is subsequently processed by the processor arrangement 50 in operation 107, with the processor arrangement 50 controlling the display device 40 in operation 109 to display the ultrasound image generated from the received ultrasound data generated with the ultrasound probe 10.

Figure 6:
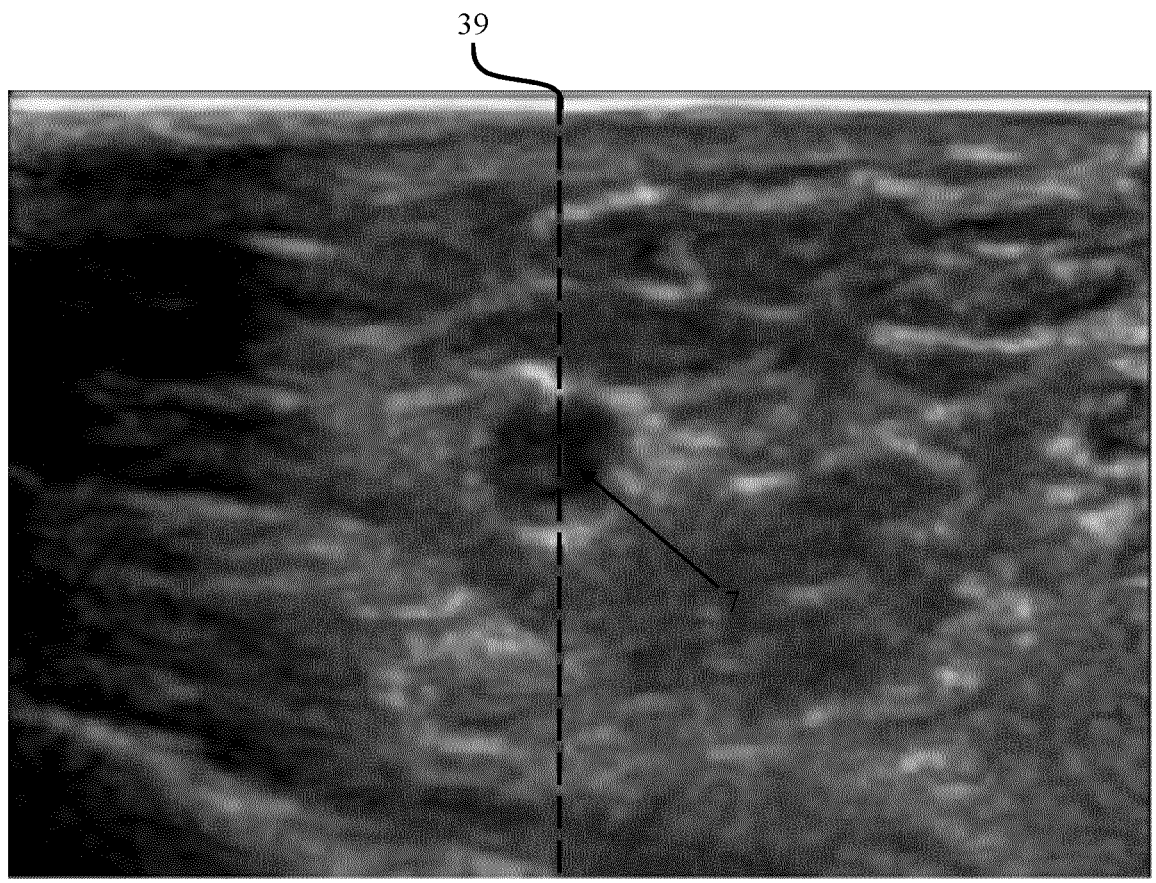
FIG. 6 schematically depicts a method of marking a displayed ultrasound image according to an embodiment.
Figure 6:
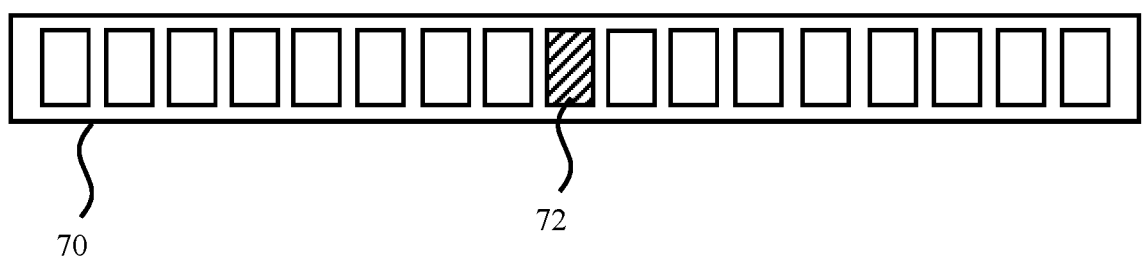

In operation 111, the processor arrangement 50 receives a selection signal generated with the user interface 38, which selection signal corresponds to a user of the user interface 38 marking a region of a displayed ultrasound image as schematically depicted in FIG. 6. In FIG. 6, the user has marked a central region of an anatomical feature 7, here a blood vessel by way of non-limiting example, by way of drawing a vertical line across the displayed ultrasound image using the user interface 38. Of course, it should be understood that the region of interest of the displayed ultrasound image may be marked using any suitably shaped marker, e.g. a solid or dashed line, a polygonal shape such as a triangle, rectangle and so on, a continuous shape such as a circle or oval, etcetera. A line is preferred as it more intuitively corresponds to a column or row of pixels (or voxels) generated by an individual transducer element 66 of the ultrasound probe 10.

In operation 113, the processor arrangement 50 identifies the individual transducer element 66, or the scan line of transducer elements, responsible for the generation of the marked region of the displayed ultrasound image. Optionally, the processor arrangement 50 in operation 115 may further identify the light source 72 associated with the identified transducer element 72, in which case the processor arrangement 50 may send a light source selection signal to the controller 80 of the light sources 72 in which the actual light source 72 to be enabled is identified. However, the processor arrangement 50 may be unaware of the mapping between light sources 72 and transducer elements 66 at the ultrasound probe 10. In the latter scenario, operation 115 may be skipped, with the processor arrangement instead sending a light source selection signal to the controller 80 identifying the individual transducer element 66 responsible for the generation of the marked region of the displayed ultrasound image in operation 119, with the controller 80 possessing the mapping information based on which the appropriate light source 72 corresponding to the identified transducer element 66 may be identified and activated (switched on) in operation 121, as schematically depicted in FIG. 6 by the shaded light source 72 in the array 70 below the ultrasound image.

Figure 7:
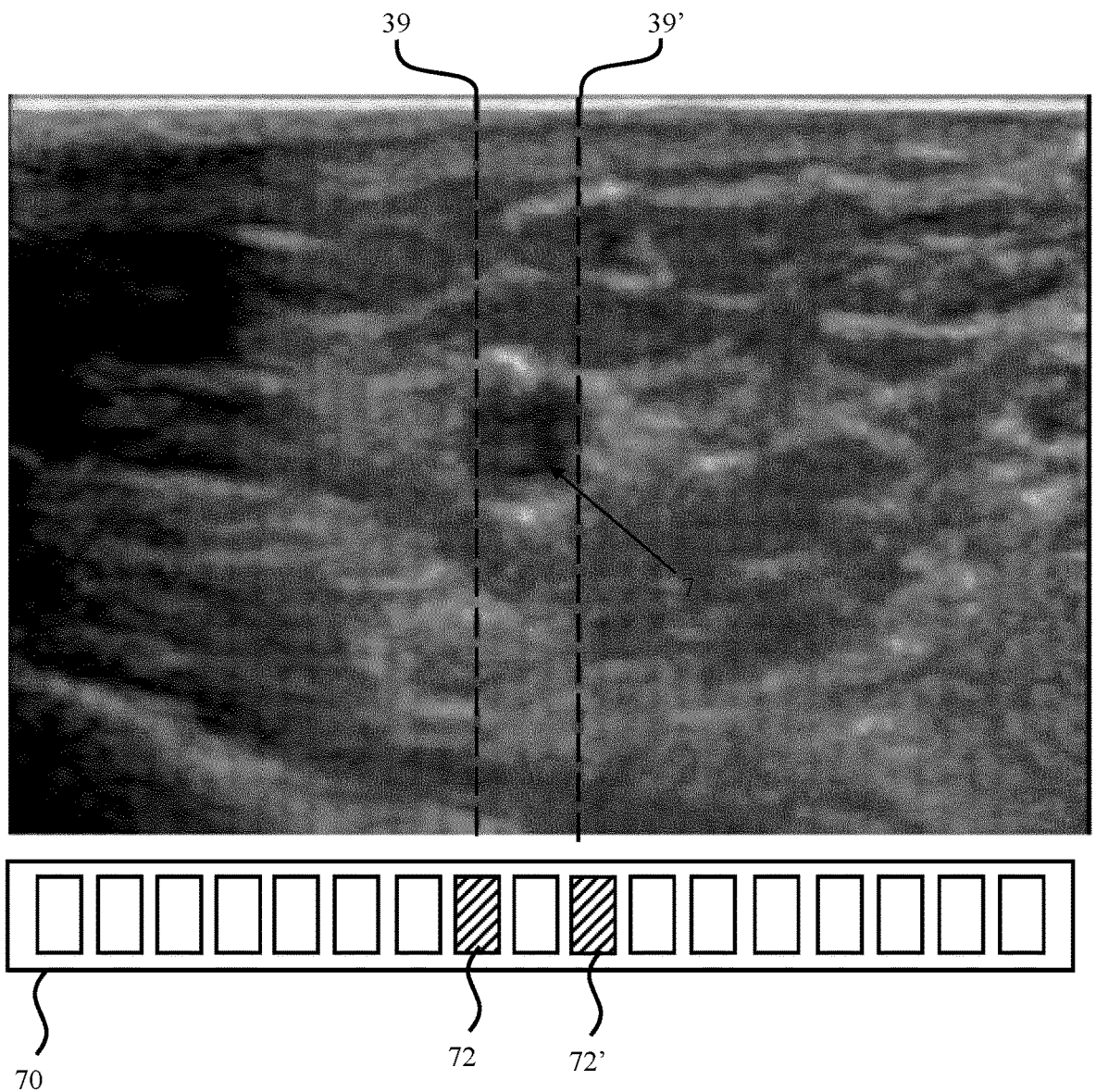
FIG. 7 schematically depicts a method of marking a displayed ultrasound image according to another embodiment.

In operation 117, it is checked if the user has marked all regions of interest, e.g. by detection of a user selecting a 'complete' operation or the like, by detection of a user exiting an ultrasound image region marking function, and so on. For example, where the user is interested in marking a central region of the anatomical feature 7 in the displayed ultrasound image, the user typically will mark only one region of the displayed ultrasound image. However, as schematically depicted in FIG. 7, the user may instead want to mark opposite edges or boundaries of the anatomical feature 7, as indicated by lines 39 and 39', such that the processor arrangement 50 identifies a pair of ultrasound transducers 66 responsible for the generation of the ultrasound image regions marked by lines 39 and 39' respectively. This will cause the generation of a light source selection signal in which the pair of (scan lines of) transducer elements 66 or associated light sources 72 are identified, or cause the generation of a pair of light source selection signals each identifying one of the (scan lines of) transducer elements 66 or associated light source 72 of this pair in operation 119 upon completion of the user marking the displayed ultrasound image as detected in operation 117. This will cause the illumination (switching on) of a pair of light sources 72, 72' in the array 70 in operation 121 as schematically depicted in FIG. 7, which light sources mark the physical location of the opposite edges or boundaries of the anatomical feature 7 below the patient contact surface 65 of the ultrasound probe 10, such that the physician can align an invasive medical instrument with the anatomical feature 7 by positioning the invasive medical instrument in between the illuminated light sources 72, 72' of the array 70. Subsequently, the method 100 may terminate in operation 123.

In a further refinement, once the user has marked the region of interest, the position of the ultrasound probe 10 relative to the marked region of interest may be tracked, e.g. when the ultrasound probe 10 is translated across the patient's anatomy. This for instance may be achieved using a simple tracking algorithm utilizing image characteristics, such as for example image intensity, in which the image characteristics of the marked region (or multiple marked regions) are identified and tracked across subsequent ultrasound images, e.g. by identifying the region in such a subsequent ultrasound image having a substantially similar shape and image characteristics as the marked region(s) in the original ultrasound image. For a vascular system, this means that such tracking can track the location of an artery or the like within an ultrasound image generated with the ultrasound probe 10 if the ultrasound probe is slightly moved, e.g. by tracking the user-highlighted region of interest based on the image characteristics such as intensity values of the pixels (or voxels) of the selected region(s) and automatically adjust which light source(s) 72, 72' are to be activated on the ultrasound probe 10 based on the movement of the highlighted region(s) of interest between successive ultrasound images, e.g. displacement of the highlighted region(s) of interest relative to the selected position of the highlighted region(s) of interest in the original ultrasound image.

It should be understood that the above described embodiment of method 100 is by away of non-limiting example only and that many variations will be immediately apparent to the skilled person. For instance, in case of the generation of multiple markers in the displayed ultrasound image by the user of the ultrasound user console 3, the light source selection signals sent to the controller 80 in operation 119 may be sent prior to completion of operation 117, e.g. after each marker generated by the user of the ultrasound user console. Such variations form part of the teachings of the present application.

As discussed above, the processing unit, for instance a controller implements control method(s). The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

As shown, the processor arrangement 50 may include one or more discrete processors. These elements may be in direct or indirect communication with each other, for example via one or more buses.

Processor per the present disclosure, such as the processor arrangement 50, may include a central processing unit (CPU), a digital signal processor (DSP), an ASIC, a controller, an FPGA, another hardware device, a firmware device, or any combination thereof configured to perform the operations described herein. Such processor may also be implemented as a combination of computing devices, e.g., a combination of a DSP and a microprocessor, a plurality of microprocessors, one or more microprocessors in conjunction with a DSP core, or any other such configuration. In some embodiments, the processor is a distributed processing system, e.g. formed of a set of distributed processors.

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller. While the invention has been illustrated and described in detail in the drawings and foregoing description, such illustration and description are to be considered illustrative or exemplary and not restrictive; the invention is not limited to the disclosed embodiments.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound probe comprising:
 a plurality of transducers within a housing and arranged proximal to a subject contact surface of the probe;
 a plurality of individually addressable light sources mounted in said housing, each of said individually addressable light sources indicating a position of a subset of the plurality of transducers relative to said subject contact surface; and
 a controller arranged to control said plurality of individually addressable light sources in response to a light source selection signal from an ultrasound user console,
 wherein the light source selection signal identifies an ultrasound transducer or a scan line of ultrasound transducers from said plurality of ultrasound transducers responsible for generating a user-marked region of a displayed ultrasound image,
 wherein the light sources are controlled to output the position of the identified ultrasound transducer or scan line relative to the subject contact surface of said probe.

2. The ultrasound probe of claim 1, wherein the individually addressable light sources are LEDs (light emitting diodes).

3. The ultrasound probe of claim 1, wherein each individually addressable light source indicates the position of a single transducer element or single scan line of transducer elements relative to said subject contact surface.

4. The ultrasound probe of claim 1, wherein the plurality of transducer elements and the individually addressable light sources each are arranged in a 1-dimensional array or a 2-dimensional array.

5. The ultrasound probe of claim 1, wherein the individually addressable light sources are arranged proximal to said subject contact surface on a side surface of the housing.

6. The ultrasound probe of claim 1, wherein the ultrasound probe is a patch and the individually addressable light sources are arranged on a portion of the housing surrounding and in the plane of said subject contact surface.

7. An ultrasound user console comprising:
 an ultrasound probe of claim 1;
 a processor arrangement adapted to convert ultrasound echo signals received by the plurality of ultrasound transducers of the ultrasound probe into an ultrasound image;
 a display under control of said processor arrangement and adapted to display said ultrasound image; and
 a user interface communicatively coupled to the processor arrangement and adapted to allow a user to mark a region of the displayed ultrasound image;
 wherein the processor arrangement further is adapted to:
 identify an ultrasound transducer or a scan line of ultrasound transducers from said plurality of ultrasound transducers responsible for generating the marked region of the displayed ultrasound image; and
 generate a light source selection signal for the light source of said ultrasound probe indicating the position of the identified ultrasound transducer or scan line relative to the subject contact surface of said probe.

8. The ultrasound user console of claim 7, wherein the user interface is adapted to allow said user to mark said region by drawing a line across said region.

9. The ultrasound user console of claim 7, wherein: the user interface further is adapted to allow a user to mark a further region of the displayed ultrasound image; and
 the processor arrangement further is adapted to:
 identify a further ultrasound transducer or further scan line of ultrasound transducers from said plurality of ultrasound transducers responsible for generating the marked further region of the displayed ultrasound image; and
 generate a further light source selection signal for the further light source of said ultrasound probe indicating the position of the identified further ultrasound transducer or further scan line relative to the subject contact surface of said probe.

10. The ultrasound user console of claim 7, wherein the processor arrangement further is adapted to:
 convert further ultrasound echo signals received by the plurality of ultrasound transducers of the ultrasound probe into a further ultrasound image;
 identify the marked region in the further ultrasound image;
 identify an ultrasound transducer or a scan line of ultrasound transducers from said plurality of ultrasound transducers responsible for generating the marked region of the further ultrasound image; and
 generate a further light source selection signal for the light source of said ultrasound probe indicating the position of the identified ultrasound transducer or scan line of ultrasound transducers responsible for generating the marked region of the further ultrasound image relative to the subject contact surface of said probe.

11. The ultrasound user console of claim 7, wherein the displayed ultrasound image is a B-mode ultrasound image.

12. A method of marking the location of an anatomical feature within a subject, the method comprising:
 generating ultrasound image data of an anatomy of the subject with an ultrasound probe, wherein said anatomy comprises the anatomical feature;
 generating an ultrasound image from said ultrasound image data and displaying said ultrasound image with an ultrasound user console
 receiving a marker marking part of said anatomical feature in said ultrasound image from a user interface of said ultrasound user console;
 identifying an ultrasound transducer or a scan line of ultrasound transducers from said plurality of ultrasound transducers responsible for generating the marked part of the anatomical feature in the displayed ultrasound image;
 generating a light source selection signal for the light source of said ultrasound probe indicating the position of the identified ultrasound transducer or scan line relative to the subject contact surface of said probe; and
 switching on said light source in response to said generated light source selection signal.

13. The method of claim 12, wherein the marked part of said anatomical feature approximates a centre line of said anatomical feature.

14. The method of claim 12, wherein the marked part of said anatomical feature approximates an edge of said anatomical feature, the method further comprising:
- receiving a further marker marking an approximate opposite edge of said anatomical feature in said ultrasound image from the user interface of said ultrasound user console;
- identifying a further ultrasound transducer or further scan line of ultrasound transducers from said plurality of ultrasound transducers responsible for generating said approximate opposite edge of the anatomical feature in the displayed ultrasound image;
- generating a further light source selection signal for the further light source of said ultrasound probe indicating the position of the identified further ultrasound transducer or further scan line relative to the subject contact surface of said probe; and
- switching on said further light source in response to said generated further light source selection signal.

* * * * *